US012411121B2

(12) United States Patent
Atluri et al.

(10) Patent No.: US 12,411,121 B2
(45) Date of Patent: Sep. 9, 2025

(54) PREDICTIVE ALERTING AND CUTOFF OF HAZARDOUS WATER FLOW

(71) Applicant: International Business Machines Corporation, Armonk, NY (US)

(72) Inventors: Dharma Teja Atluri, Hyderabad (IN); Siddhartha Sood, Ghaziabad (IN); Santanu Ghosh, Kolkata (IN); Snehasish Ghosh, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 487 days.

(21) Appl. No.: 17/361,191

(22) Filed: Jun. 28, 2021

(65) Prior Publication Data

US 2022/0412512 A1 Dec. 29, 2022

(51) Int. Cl.
*G06F 3/048* (2013.01)
*G01N 33/18* (2006.01)
(Continued)

(52) U.S. Cl.
CPC ......... *G01N 33/18* (2013.01); *G05B 13/0265* (2013.01); *G06N 20/00* (2019.01)

(58) Field of Classification Search
CPC .... G06N 20/00; G05B 13/0265; G05B 15/02; G05B 19/042; G05B 19/416; G05B 19/0428; G05B 19/05; G05B 19/0426; G05B 19/0423; G05B 13/04; G05B 13/021; G05B 13/024; G05B 13/042; G05B 13/048; G05B 13/041; G05B 13/02; G05B 11/01; G05B 11/42; G05B 2219/37371; G05B 2219/2625; G05B 2219/2642; G05B 2219/45006; G05B 2219/41303;
(Continued)

(56) References Cited

U.S. PATENT DOCUMENTS 8,377,314 B2 2/2013 Frank
8,486,275 B2 7/2013 Wolf
(Continued)

FOREIGN PATENT DOCUMENTS

CN 103175513 B 11/2013
CN 102053139 B 6/2014
(Continued)

OTHER PUBLICATIONS

International Search Report and Written Opinion, International Application No. PCT/EP2022/065963, International Filing Date Jun. 13, 2022.
(Continued)

*Primary Examiner* — Aleksey Olshannikov
(74) *Attorney, Agent, or Firm* — Heather Johnson

(57) ABSTRACT

A system may include a memory and a processor in communication with the memory. The processor may be configured to perform operations. The operations may include accepting fluid parameter data about a fluid and identifying at least one safety threshold for the fluid. The operations may further include calculating a fluid quality index for the fluid based on the fluid parameter data and analyzing the fluid quality index against the at least one safety threshold to achieve fluid quality testing data. The operations may also include leveraging the fluid quality testing data to control a fluid flow.

20 Claims, 11 Drawing Sheets

(51) Int. Cl.
*G05B 13/02* (2006.01)
*G06N 20/00* (2019.01)

(58) Field of Classification Search
CPC ...... G05B 17/02; G05B 9/02; G05B 23/0283; G05B 23/0235; G01N 33/18–1893; G05D 7/00–0694; G05D 11/00–16; G06Q 50/06
See application file for complete search history.

(56) References Cited

U.S. PATENT DOCUMENTS

| | | | |
|---|---|---|---|
| 2002/0002425 A1 | 1/2002 | Dossey | |
| 2008/0082215 A1 | 4/2008 | McDowell | |
| 2008/0150750 A1* | 6/2008 | Parris | G01D 11/245 73/201 |
| 2009/0099700 A1 | 4/2009 | Taravat | |
| 2014/0052422 A1* | 2/2014 | Wan | C02F 3/006 703/2 |
| 2014/0278246 A1* | 9/2014 | Clark | G01N 33/18 702/182 |
| 2014/0373926 A1* | 12/2014 | Jha | G01N 33/18 702/182 |
| 2017/0185892 A1* | 6/2017 | Han | C02F 3/006 |
| 2018/0311663 A1 | 11/2018 | Giera | |
| 2018/0348190 A1* | 12/2018 | Whiting | G01N 33/2835 |
| 2019/0318605 A1* | 10/2019 | Manoria | G01N 33/18 |
| 2019/0332990 A1* | 10/2019 | Klicpera | G06Q 30/0234 |
| 2020/0003646 A1 | 1/2020 | Krywyj | |
| 2021/0071379 A1* | 3/2021 | Allara | G08B 21/182 |
| 2021/0375440 A1* | 12/2021 | Schlameuss | G01N 33/18 |

FOREIGN PATENT DOCUMENTS

| | | |
|---|---|---|
| CN | 102539643 B | 2/2017 |
| CN | 105092811 B | 2/2017 |
| IN | 202041003470 A | 2/2020 |

OTHER PUBLICATIONS

Anonymous. "2012 Drinking Water—Specification." Published May 2012. 16 pages. Published by Bureau of Indian Standards. http://cgwb.gov.in/Documents/WQ-standards.pdf.
Anonymous. "A System and Method to Provide a Cognitive, IoT—Analytics-Based Solution which Collects Data Used to Predicatively Regulate and Track Water Consumption for Livestock and Dairy Management." Published Jan. 24, 2019. 6 pages. Published by IP.com. https://priorart.ip.com/IPCOM/000257247.
Anonymous. "Chemical fact sheets." Accessed May 13, 2021. 147 pages. Published by World Health Organization. https://www.who.int/water_sanitation_health/publications/gdwq4-with-add1-chap12.pdf?ua=1.
Anonymous. "Goal 6: Ensure access to water and sanitation for all." Printed May 13, 2021. 7 pages. Published by UN.org. https://www.un.org/sustainabledevelopment/water-and-sanitation/.
Anonymous. "India Water Resources Information System." Printed May 13, 2021. 4 pages. Published by NWIC. https://indiawris.gov.in/wris/#/.
Anonymous. "Real time detection and isolation of water pollution sources using IoT and Cognitive technology." Published May 4, 2018. 5 pages. Published by IP.com. https://priorart.ip.com/IPCOM/000253799.
Anonymous. "Water sanitation hygiene." Printed May 13, 2021. 2 pages. Published by World Health Organization. https://www.who.int/water_sanitation_health/diseases-risks/en/.
Anonymous. "Your housing community could be saving upto 50% water." Printed May 13, 2021. 9 pages. Published by WEGOT. https://www.wegot.in/residential.html.
Daigavane, et al., "Water Quality Monitoring System Based on IOT." Published in 2017. 10 p. In Advances in Wireless and Mobile Communications. ISSN 0973-6972 vol. 10, No. 5 (2017), pp. 1107-1116. Published by Research India Publications. https://www.ripublication.com/awmc17/awmcv10n5_24.pdf.
Mell, et al., "The NIST Definition of Cloud Computing," Recommendations of the National Institute of Standards and Technology, U.S. Department of Commerce, Special Publication 800-145, Sep. 2011, 7 pgs.

* cited by examiner

PREDICTIVE ALERTING AND CUTOFF OF HAZARDOUS WATER FLOW

BACKGROUND

The present disclosure relates to water processing and more specifically to predicting water quality.

Maintaining good water quality for human consumption is a challenge communities face, threatening human health, limiting food production, reducing ecosystem functions, et cetera. The presence of microbes and the presence of chemicals are the two largest causes of water-borne ailment, at least some of which is the result of unsafe water supply.

SUMMARY

Embodiments of the present disclosure include a system, method, and computer program product for monitoring water quality and enabling responses to changes in water quality.

A system in accordance with the present disclosure may include a memory and a processor in communication with the memory. The processor may be configured to perform operations. The operations may include accepting fluid parameter data about a fluid and identifying at least one safety threshold for the fluid. The operations may further include calculating a fluid quality index for the fluid based on the fluid parameter data and analyzing the fluid quality index against the at least one safety threshold to achieve fluid quality testing data. The operations may also include leveraging the fluid quality testing data to control a fluid flow.

The above summary is not intended to describe each illustrated embodiment or every implement of the disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
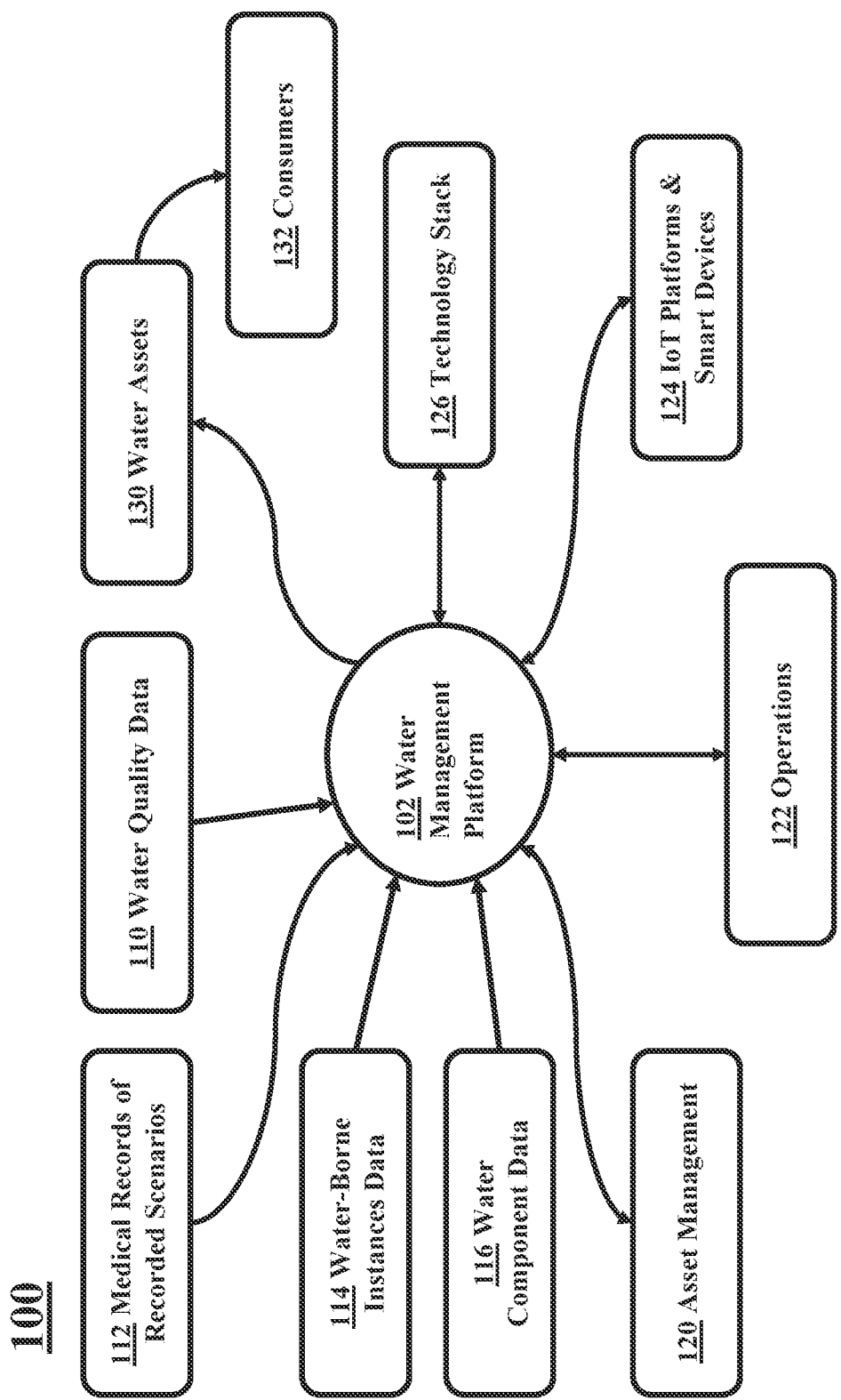
FIG. 1 illustrates a context diagram of a water management system in accordance with some embodiments of the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to water processing and more specifically to monitoring water quality. The present disclosure may be used to predict the adverse effects of consumption of certain water supplies and thereby stop possible contamination by cutting off the supply of the dubious water until it can be tested and/or purified.

A system in accordance with the present disclosure may include a memory and a processor in communication with the memory. The processor may be configured to perform operations. The operations may include accepting fluid parameter data about a fluid and identifying at least one safety threshold for the fluid. The operations may further include calculating a fluid quality index for the fluid based on the fluid parameter data and analyzing the fluid quality index against the at least one safety threshold to achieve fluid quality testing data. The operations may also include leveraging the fluid quality testing data to control a fluid flow.

In some embodiments of the present disclosure, the fluid flow is stopped if the fluid quality testing data is not within the at least one safety threshold (e.g., a particular substance level is over a predetermined parts per million (PPM) level, et cetera).

Some embodiments may further include generating an alert based on the fluid quality testing data and publishing the alert (e.g., sending a push-message to a user, posting a message on a municipality webpage, et cetera). In some embodiments, the alert identifies the fluid quality testing data exceeds at least one safety threshold and the alert triggers a stoppage of the fluid flow.

In some embodiments of the present disclosure, a machine learning model calculates the fluid quality testing data. In some embodiments, the machine learning model calculates the fluid quality testing data in real time (e.g., the fluid quality testing data can be calculated simultaneously, or substantially close to simultaneously, with data input).

Some embodiments of the present disclosure may further include capturing current fluid parameter data with at least one fluid monitoring device. In some embodiments, the fluid monitoring device is a smart water meter.

The present disclosure leverages cloud platform services. Internet of things (IoT) data may be integrated into relevant machine learning processes from information gathering equipment. Information gathering equipment may include, for example, smart meters, smart sensors (including sensors capable of estimating microbe concentration), and other electronic devices which may enable the continuous measurement and correlation of water quality. A standardized index may be used to rate water quality such as standards established by various governmental directives such as the Indian Standard for Drinking Water Specification as set by the Bureau of Indian Standards, the Safe Water Drinking Act in the United States, and the European Drinking Water Directive in Europe, as well as those set by the World Health Organization (WHO) and other international groups.

Based on real time water quality index check, proactive corrective measures may be triggered to prevent unsafe drinking water from being supplied thereby containing the spread of water borne diseases. Such water quality parameters and especially early corrosion detection can help identify asset failures beforehand. Detection of failures beforehand will also help prevent microbe contamination at such sites The present disclosure leverages cloud platform services, machine learning on IoT data (which may be integrated from equipment including smart meters, smart sensors which may have the capability to estimate bacteria concentration, and modern electronic devices) to ensure continuous measurement and correlation of water quality. Water quality may be indexed with reference to standards prescribed by specific organizations, institutions, or governments. For example, the WHO prescribed standards may be used as reference standards. Proactive corrective measures may be triggered based on real time water quality index checks to prevent unsafe drinking water from being supplied to consumers, thereby containing the spread of water borne infections. Water quality parameters and early corrosion detection can help identify asset failures beforehand to prevent downstream problems. Detection of failures beforehand may also help prevent microbe contamination at affected sites.

The present disclosure may use an IoT and machine learning (ML) system monitoring of various water parameters such as inflow, outflow, physical properties (e.g., temperature and turbidity), chemical properties (e.g., pH and concentrations such as chloride, nitrate, sulphate, and total dissolved solids (TDS) concentrations), and microbial properties (e.g. giardia, salmonella, et cetera). The water quality index (chemical and microbial both) may be compared against benchmark levels and used to build a classification model to predict water-borne instances (e.g., instances of water-borne diseases or water-borne infections).

The data may be collected and stored in a water quality database. The data may contain, for example, information about chemical and microbial properties which may be stored as a binary classifier. The water quality database may be implemented and maintained using established quality standards of accredited organizations (e.g., the WHO, a scientific group, a government, or a government agency) for drinking water or sewage water. The data may be collected by smart IoT sensors which may be implemented at supply points (e.g., source, treatment, and distribution centers) of various water assets. Such supply points could be, for example, pump stations, water storage units, households, and other places that supply, store, treat, and/or distribute water.

There may be a standard ML classifier running at regular intervals (e.g., time of supply, filtration, distribution, et cetera) and predict if the inflow and outflow water quality can cause water-borne infection. Predictions detected at source, storage, treatment, and distribution locations (measured with reference to the standards maintained in the database) may generate an electronic signal from an IoT based sensor which may trigger an electronic circuit breaker to cut off the water supply in and out of the impacted asset. To keep the model updated, a feedback loop may be implemented to ensure new data points are constantly fed into the water quality database to aid future predictions and increase the confidence level of the predictions. This could initially be a supervised learning model to pick up based on further training to reach the next stage.

Initial labeling could be based on known water standards or patterns. Specifically, labeling could start with information about what infections have been triggered and what water qualities (e.g., the chemical/microbial mix) were associated with the infections. For more comprehensive labeling, academic and research institute data could be involved, and quantum computing services could be leveraged to validate and breakdown the chemical composition. This can feed into the water quality database as a baseline. In some embodiments of the present disclosure, a continuous improvement process can be implemented to ensure newly identified microbial infection or harmful chemical composition is immediately updated into the database.

In some embodiments, the present disclosure provides a water quality and water supply control mechanism which may integrate various existing methods, mechanisms, and processes into a comprehensive packaged solution that can be implemented to predict issues related to water quality for water assets and trigger preventive and/or corrective actions. The present disclosure can integrate modern technology stacks and assets to form a water quality management platform. The present disclosure be implemented for any water asset. Modifications may be made to integrate it into applications which may require such modifications for implementation while remaining in accordance with the present disclosure.

A database of water quality parameters may be maintained. Various water quality and related information is gathered by various agencies for numerous water assets, but it may be difficult to comprehend both incidence and type of disease, resulting in difficulty leveraging the data as an asset. The present disclosure discusses maintaining a database containing a list of various information necessary and/or helpful in relating the data to consequences. The database may contain information such as the physical properties of water quality (e.g., temperature and turbidity), chemical characteristics/parameters (e.g., pH and dissolved oxygen), and microbial indicators of water quality (e.g., bacteria and viruses). These parameters may be checked against permissible levels as defined by standards organizations specific to local (e.g., regional) scenarios.

These parameters are relevant to groundwater and industrial processes as well as surface water studies of the ocean, lakes, rivers, et cetera. The data may be augmented by linking the quality parameters with the incidence of disease and possible type or types of disease. The data may be continuous evolving as and when new incidences associated with water quality indices are discovered. In some embodiments, quantum computing may be leveraged to break down the chemical composition on a real time basis based on different contamination scenarios; this information may be continuously fed into the water quality database. In some embodiments, an open source approach may be used to get institutes and individuals to update information based on local environmental conditions in the ecosystem such that various sources may contribute to the database (e.g., crowd source information). A common platform service may be used to facilitate such an embodiment.

Disease incidence classification may also depend on other variables like total daily intake (TDI) of water, presence of comorbidities, et cetera. The impact of these variables on incidence classification could be baselined. Additionally, feature selection may be used in leveraging statistical methods to identify the optimal set of objective and subjective variables. Further, water related parameters may be collected by various independent agencies across thousands of assets, and these parameters may also be staged in the same database on regular intervals.

Incoming water may be measured against quality parameters from a chemical and microbial perspective. Multiple water quality indices may be used. For example, a chemical quality index (CQI) and a microbial quality index (MQI) may be used. The water quality database may track incidences (e.g., incidences of disease, such as whether any outbreak occurred at the time certain quality measures were tracked). Feature selection may be used to check which inputs are relevant for the classification problem. Comparisons may be made between feature selections and/or feature selection methods to discover and utilize the most influencing features. The evolving dataset and its corresponding ML algorithm(s) may be trained using the database to generate an initial classifier. Various techniques may be used for such training including widely available techniques such as support vector machines, artificial neural networks, random decision forests, and the like. A baseline performance and test harness strategy may be decided, and the performance may be evaluated using standard measures such as specificity, sensitivity, area under the curve (AUC), and the like. The best performing model may be used and validated. For non-linear scenarios, ensemble learning techniques may be used if the model changes significantly with incremental changes in data.

An incidence algorithm may be executed at supply, storage, treatment, and/or filtration points. The output may be monitored. If the standards are not met and there is an unacceptable possibility of outbreak, the system may trigger necessary actions for the water valves (which may be operated as circuit-breakers) to disengage and stop water supply to prevent contamination of drinking water. Such data supported decisions can help initiate various programs (e.g., social and/or governmental programs) to perform checks on sources of contamination as well as ways to reduce risk in incidences in future.

Alternate water sources may be arranged so that the risk of no/reduced water supply is preempted. For example, supply sources not likely to cause incidents may be used instead of an identified compromised source using external certified water tankers. Additionally, informing the community about possible disruption may allow for better planning and water conservation. The earlier the detection of potential instances (e.g. at treatment instead of distribution), the better it could be in terms of planning; earlier detection could also mean a wider impact. An alerting system can be used to publish alerts which can be subscribed by several subscribers such as external water providers, government blockchain platforms, municipal bodies, and the like. By detecting potential instances and providing such alerts, the burden on medical infrastructure can be reduced, cost savings can be realized by authorities, and consumers can make informed decisions.

Water quality sensors can measure multiple physical and chemical properties at the same time for water and send that information to be processed and staged in the water quality database. These sensors can be mass produced to make them widely available for implementation in various settings such as at water sources, in treatment plants, and in households. Sensors that detect physical, chemical, and/or microbial properties may be used. Water parameters could include measurements and presence and/or concentration information for several different properties such as, for example, algae, phytoplankton, chlorophyll, dissolved organic matter (DOM), conductivity, salinity, total dissolved solids (TDS), dissolved oxygen, nutrients (e.g., phosphorous, nitrogen, nitrate, and ammonia), pH, solar radiation, photosynthetically active radiation, turbidity, clarity, total suspended solids, water temperature, and the like.

Meters such as smart meters can be integrated to measure inflow and outflow water parameters. Metered parameters might include, for example, water supplied and the water pressure at the supply point. Using such meters may assist in identifying possible water loss by leakage and contamination of drinking water by external elements. A water meter may be used to measure the quantity (volume) of water that passes through a pipe or outlet. Meters may use a standard unit of measure for volume (e.g., cubic feet or gallons). A meter may work by recording the cumulative amount of water that has passed through or by the meter.

In some embodiments, an automatic on/off valve mechanism may be implemented in accordance with the present disclosure. The results of the ML algorithm may trigger an electronic signal which may turn off one or more water supply valves and raise alerts to, for example, consumers and authorities such that they may take remediating actions. Corrective action (e.g., cutting off water supply) may enable alternative water supply based on various parameters. The alerts may be integrated with other systems such as work management systems and social media sites. Alerts may also automatically trigger work orders and/or investigations into the root cause so the issue may be properly corrected.

The present disclosure may refer to fluid, fluids, or water specifically. Those skilled in the art will recognize that the present disclosure may be used for quality checking non-water fluid substances. For example, the present disclosure may also be used for identifying the solutes in a solvent, such as checking impurities in a fuel pipeline that may or may not change the way the fuel may be consumed by a fuel-powered engine or the impact certain impurities in the fuel may have on the fuel-powered engine if consumed. The term fluids may also be used to identify the product of an unknown source, or a source known to be water that requires filtration and treatment.

FIG. 1 illustrates a context diagram of a water management system 100 in accordance with some embodiments of the present disclosure. Information is fed into a water management platform 102. The information may include, for example, water quality data 110 (e.g., established standards from agencies and publications), medical records of recorded scenarios 112 (e.g., hospital records concerning water-borne incidents), water-borne instances data 114 (e.g., data from one or more health and/or environmental departments/agencies), and water component data 116 (e.g., the chemical breakdown of the water for the locale).

The water management platform 102 may exchange information with various sources including, for example, the authorities involved with asset management 120 (e.g., medical and/or personnel involved in remediation and follow up actions to be taken given specified triggers), operations 122 (e.g., personnel processing and/or completing work orders), one or more IoT platforms and smart devices 124 (e.g., exchanging measurement information), and one or more technology stacks 126 (e.g., exchanging measurement parameters).

The water management platform 102 may be used to control water assets 130 that may be distributed to various consumers 132. The water management platform 102 may control water assets 130 by, for example, sending warnings about potentially infectious water to consumers 132 and authorities or automatically turning off access to certain water assets 130 which have achieved thresholds of unacceptable risk of contamination. Consumers 132 may include, for example, domestic consumers such as families accessing water assets 130 from their household tap, corporate consumers accessing water assets 130 at work facilities, organizations using water assets 130 for charitable activities, groups using water assets 130 for social activities, governmental agencies gathering water assets 130 to distribute to citizens, and the like.

Figure 2A:
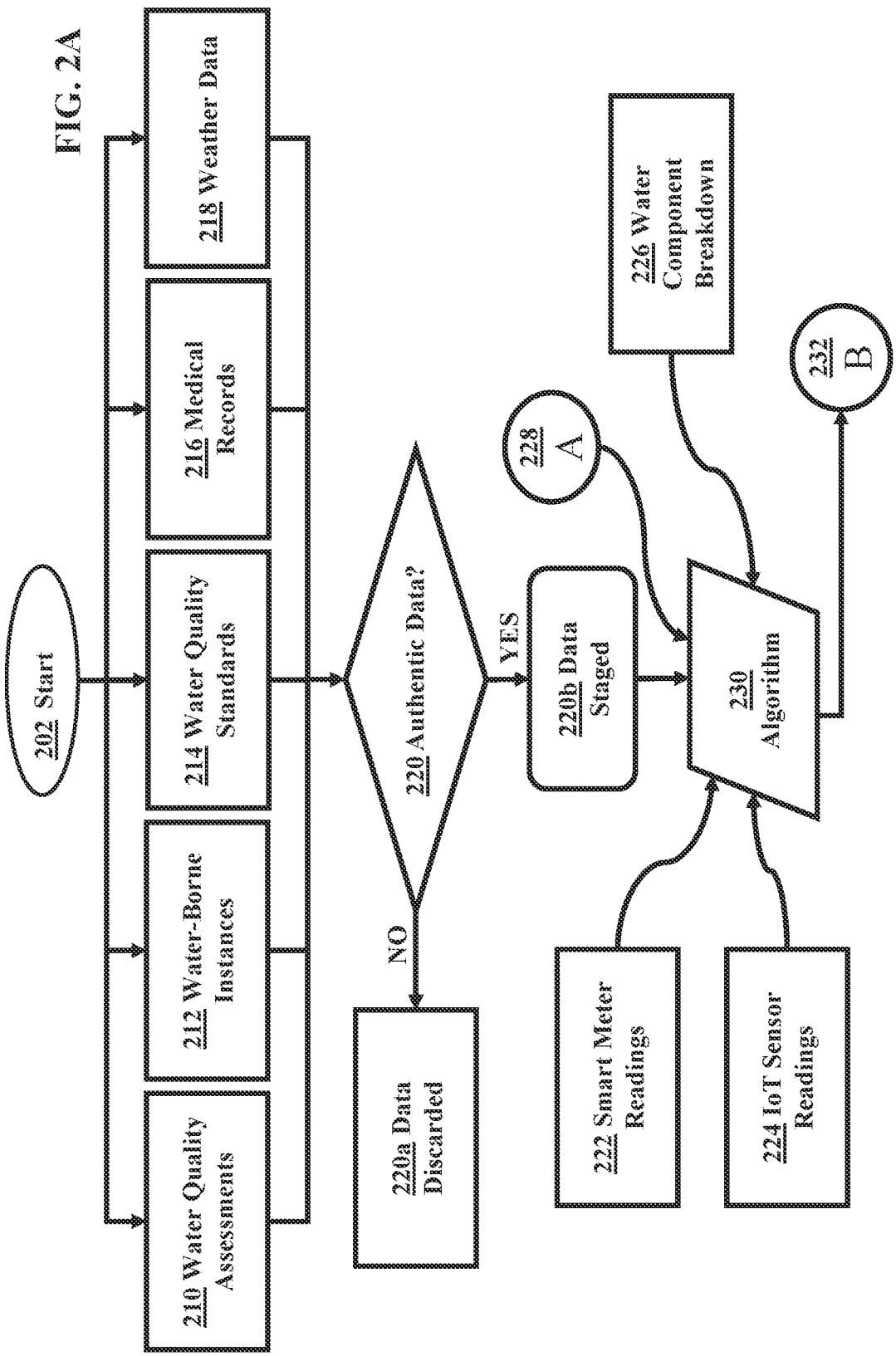
FIG. 2A depicts a system and method flow in accordance with some embodiments of the present disclosure.
Figure 2B:
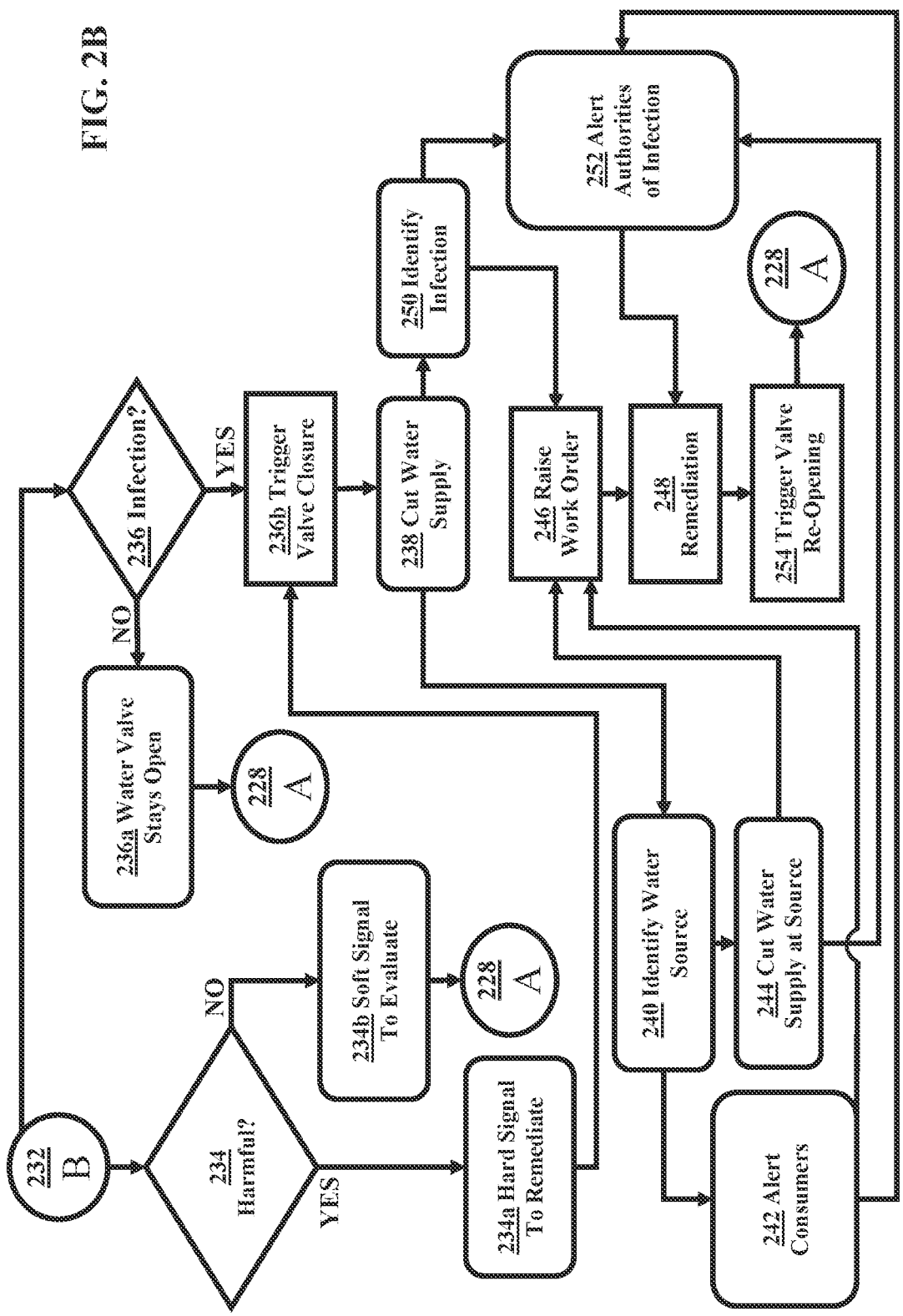
FIG. 2B illustrates a system and method flow in accordance with some embodiments of the present disclosure.

FIG. 2A and FIG. 2B depict a system and method flow in accordance with some embodiments of the present disclosure. At a start point 202, data is fed into a system. The data may include water quality assessments 210, water-borne instances data 212, water quality standards 214, medical records 216, and weather data 218. Additional information may also be included. The data is fed through an authenticity checkpoint 220. If the data is identified as authentic, the data is staged 220b (e.g., in a regional water quality data database). If the data is identified to not be authentic, the data is discarded 220a.

Authenticity of data may be determined through various means. In some embodiments, data may be accepted as authentic if it is submitted by or through a verified account (e.g., requiring a login to a website). In some embodiments, data may be accepted as authentic if it is submitted from a registered internet protocol (IP) or media access control (MAC) address. In some embodiments, data may be accepted as authentic because multiple sources (e.g., several different IP addresses) submit similar data at approximately the same time. Other methods of verifying the authenticity of data as known in the art may also be used.

Once data is verified as authentic at the authenticity checkpoint 220, the data is staged 220b and may be submitted to an algorithm 230 for processing. The algorithm 230 may be a ML algorithm. Additional data may also be fed into the algorithm 230 including, for example, smart meter readings 222, IoT sensor readings 224, water component breakdown 226, and information from a water database 228. The algorithm 230 may produce information to submit to an analysis engine 232 for analysis.

The analysis engine 232 may perform a harmfulness check 234 to evaluate whether matter identified as present in a water sample is or is likely to be harmful. The harmfulness check 234 may include, for example, whether consumption of the fluid would be harmful to humans. The harmfulness check 234 could employ hard thresholds, soft thresholds, or a combination thereof. For example, a turbidity reading could be subject to a hard threshold such that a turbidity in excess of 5 would result in a hard signal to remediate 234a and trigger valve closure 236b which would cut off the water supply 238 from the affected source; additionally, a soft threshold may be employed such that a turbidity between 0.8 and 1.2 would result in a soft signal to evaluate the situation 234b. The soft signal to evaluate the situation 234b could be fed into the water database 228.

The analysis engine 232 may perform an infectiousness check 236 to identify whether a source of water has been linked to infections (e.g., water-borne diseases, viruses, or bacteria). If no link to infection is found, the water valve stays open 236a and the information may be deposited into the water database 228. If a link to infection is discovered, it could trigger valve closure 236a which would cut off water supply 238 from the affected source.

A cut off water supply 238 may result in one or more actions. The water source may be identified 240 so that the impacted customers could be alerted 242 and the water supply may be stopped at the source 244 for evaluation and remediation. Additionally, a cut off water supply 238 could also trigger an identification mechanism to identify the infection 250 caused by the water supply such that, for example, appropriate medicine may be supplied to the impacted area(s) as part of remediation efforts.

A work order may be raised 246 and the authorities may be notified 252. The work order may be raised 246 automatically such that the problem may be remediated 248 to properly reopen the water valve 254 and restore access thereto. Information gathered during the remediation process may be submitted to a water database 228.

Figure 3:
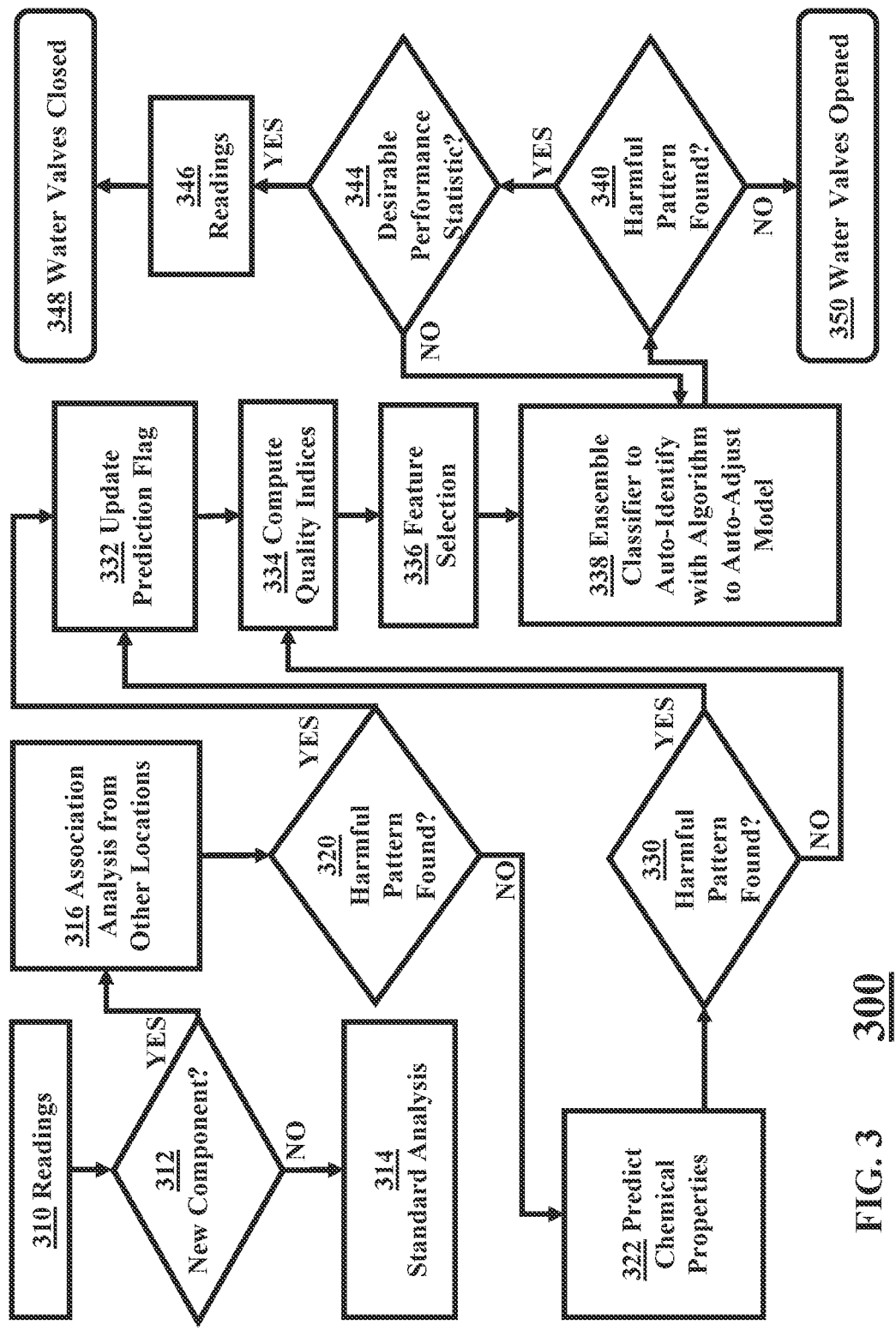
FIG. 3 depicts a system and method flow in accordance with some embodiments of the present disclosure.

FIG. 3 depicts a system and method flow 300 in accordance with some embodiments of the present disclosure. Predictions may be made as to whether or not a previously unidentified component is harmful. Readings 310 may be taken of a fluid flow. Components (e.g., solvents and solutes) may be identified. A new component check 312 may be performed to identify whether a previously unidentified component is in the fluid. Previously unidentified components may be components that are unknown or uncommon to a certain region such that the regional database does not maintain its information. If no new component is identified, the standard analysis 314 of the fluid may be performed such that the fluid is compared against known parameters. If a new component is identified, the component may be compared with external information. For example, the component may be subjected to association analysis 316 which may be completed using data from other locations.

The association analysis 316 may be used to perform a harmfulness pattern check 320. A harmfulness pattern check 320 may seek to identify whether the new component is similar to known harmful components (e.g., physical or chemical similarity with non-consumable compounds) or has been correlated with unfavorable situations (e.g., whether the new component has been present during known infections). If no harmfulness pattern is identified, chemical properties may be predicted 322 for the new component to perform a chemical properties harmfulness check 330. If no chemical harmfulness is found, quality indices may be computed 334. Various quality indices may be used as befits the particular implementation of the present disclosure. Quality indices may include, for example, chemical quality indices (CQI) and microbial quality indices (MQI).

If either the harmfulness pattern check 320 or the chemical properties harmfulness check 330 returns a result that harmfulness has been found, the prediction flag is updated 332 such that the new component will be recognized as harmful in other situations in which it is identified. The quality indices may be computed 334, and features may be selected 336 for classification. A classifier may be used to automatically adjust a model 338 which may be used to automatically monitor the fluid flow. The model may be adjusted automatically, for example, by automating the identification of new components.

In some embodiments, an ensemble classifier may be the preferred classifier. Ensemble methods may be used to identify a best fit algorithm localized for the conditions and other impacting features of the region. Using ensemble methods may enable improved predictions over other methods. Predicting the occurrences of water instances in this manner and integrating this information with the category of the instance may provide more in-depth information and enable better corrective action than a simple binary output. An ensemble classifier may be, for example, a support vector machine (SVM), an artificial neural network (ANN), a random decision forest, a deep learning neural network, or the like.

The updated model may be checked to perform a harmfulness check 340. If no harm is indicated, the water valves may be opened 350. If harm is indicated, the statistics will be checked for desirability 344 to evaluate the performance of the model. If the performance statistics are undesirable, the classifier may be used to automatically adjust the model 338 again. If the performance statistics are desirable, readings 346 may be taken to verify the harmful pattern still exists in the fluid and the water valves may be closed 348.

Figure 4:
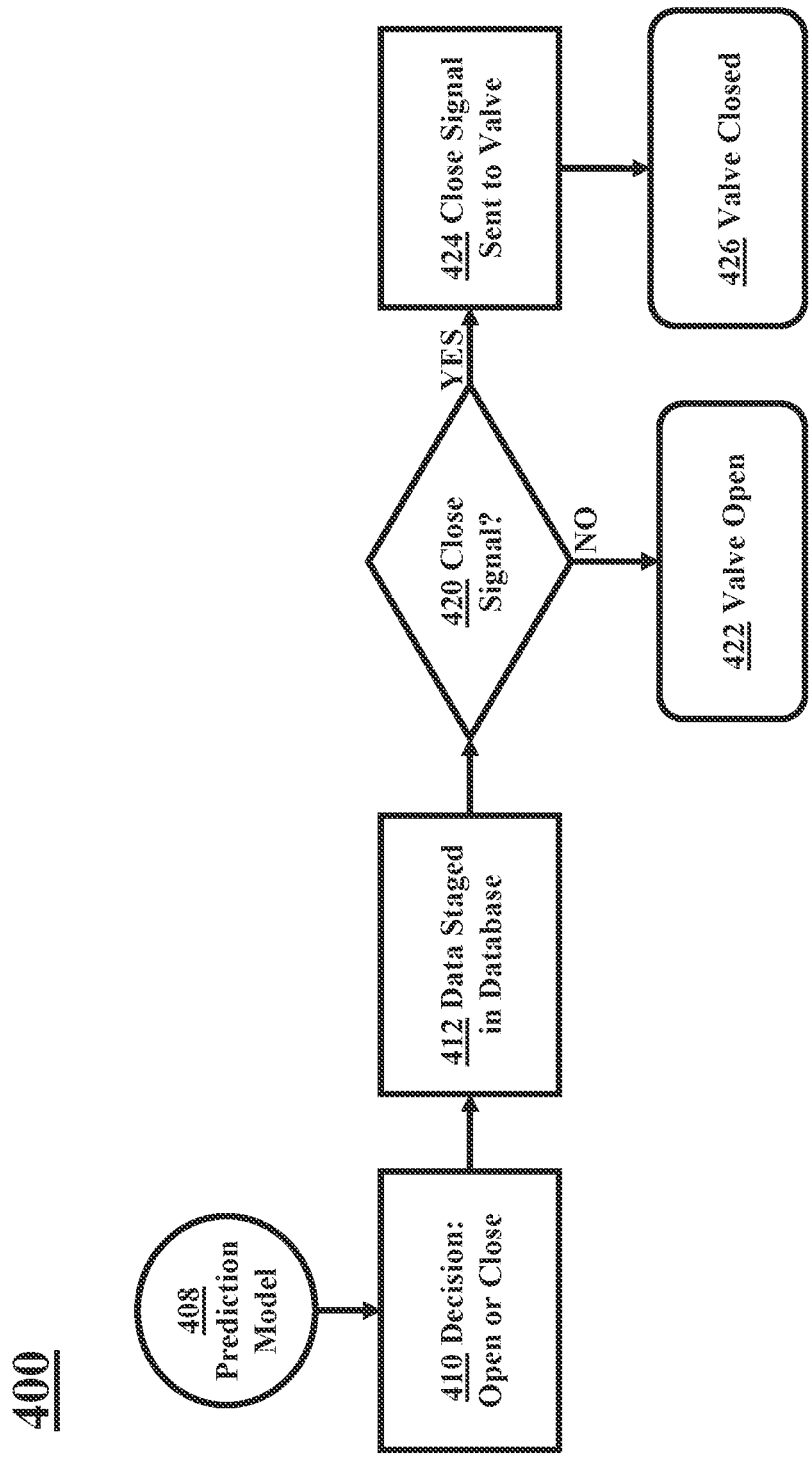
FIG. 4 illustrates a system and method flow in accordance with some embodiments of the present disclosure.

FIG. 4 illustrates a system and method flow 400 in accordance with some embodiments of the present disclosure. The system and method flow 400 has a prediction model 408 which makes a decision 410 as to whether to open or close the valves. The decision 410 and the data supporting it may be staged in a database 412. The decision 410 may be used to trigger or prevent from triggering a close signal 420. If the decision 410 prevents the triggering of a close signal, the system and method flow 400 may enable an open valve 422 such that the valve is either opened or remains opened. If the decision 410 triggers a close signal, a close signal 424 may be sent to the valve to close the valve 426.

Figure 5A:
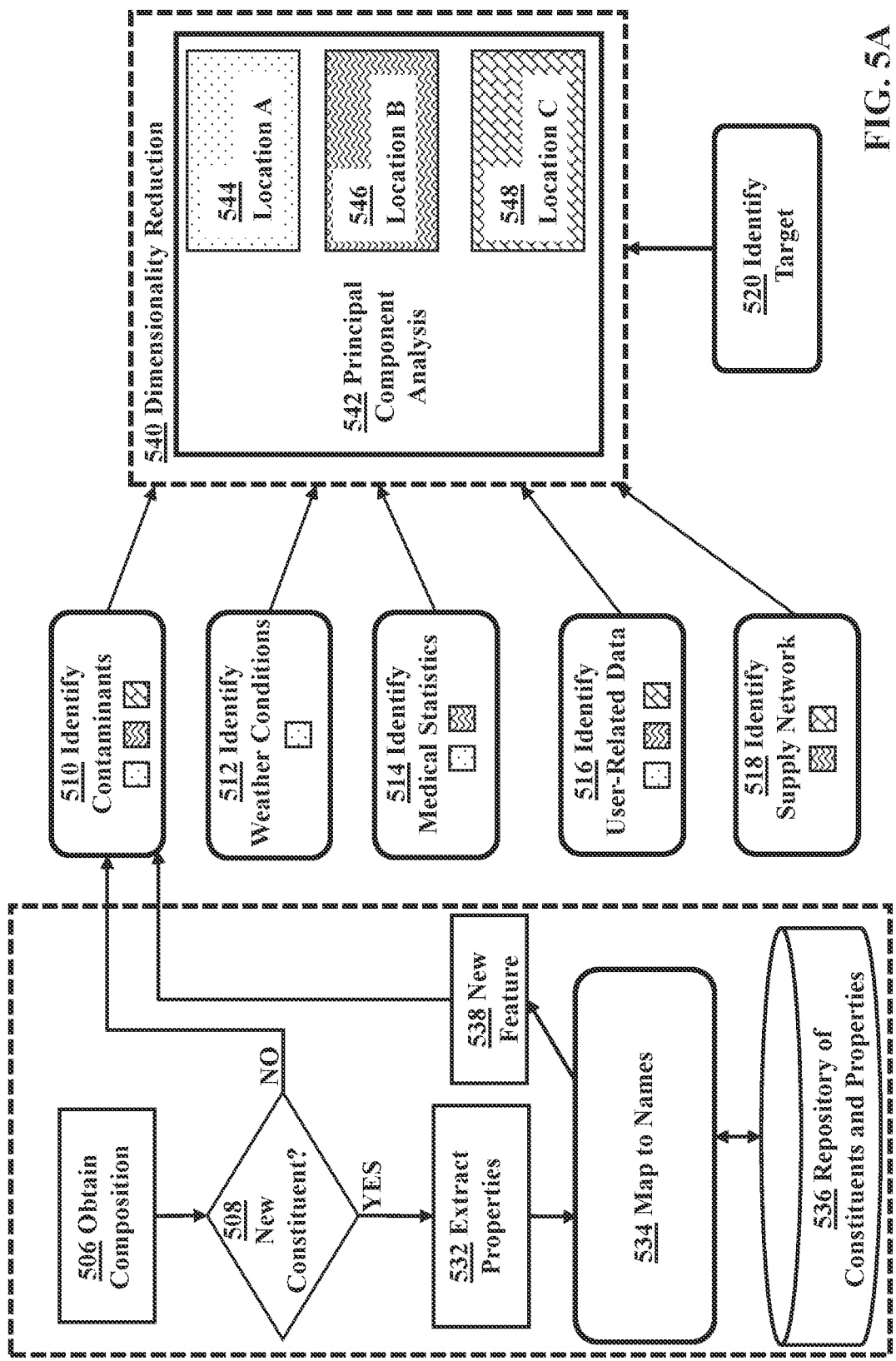
FIG. 5A depicts a workflow for incident prediction in accordance with some embodiments of the present disclosure.
Figure 5B:
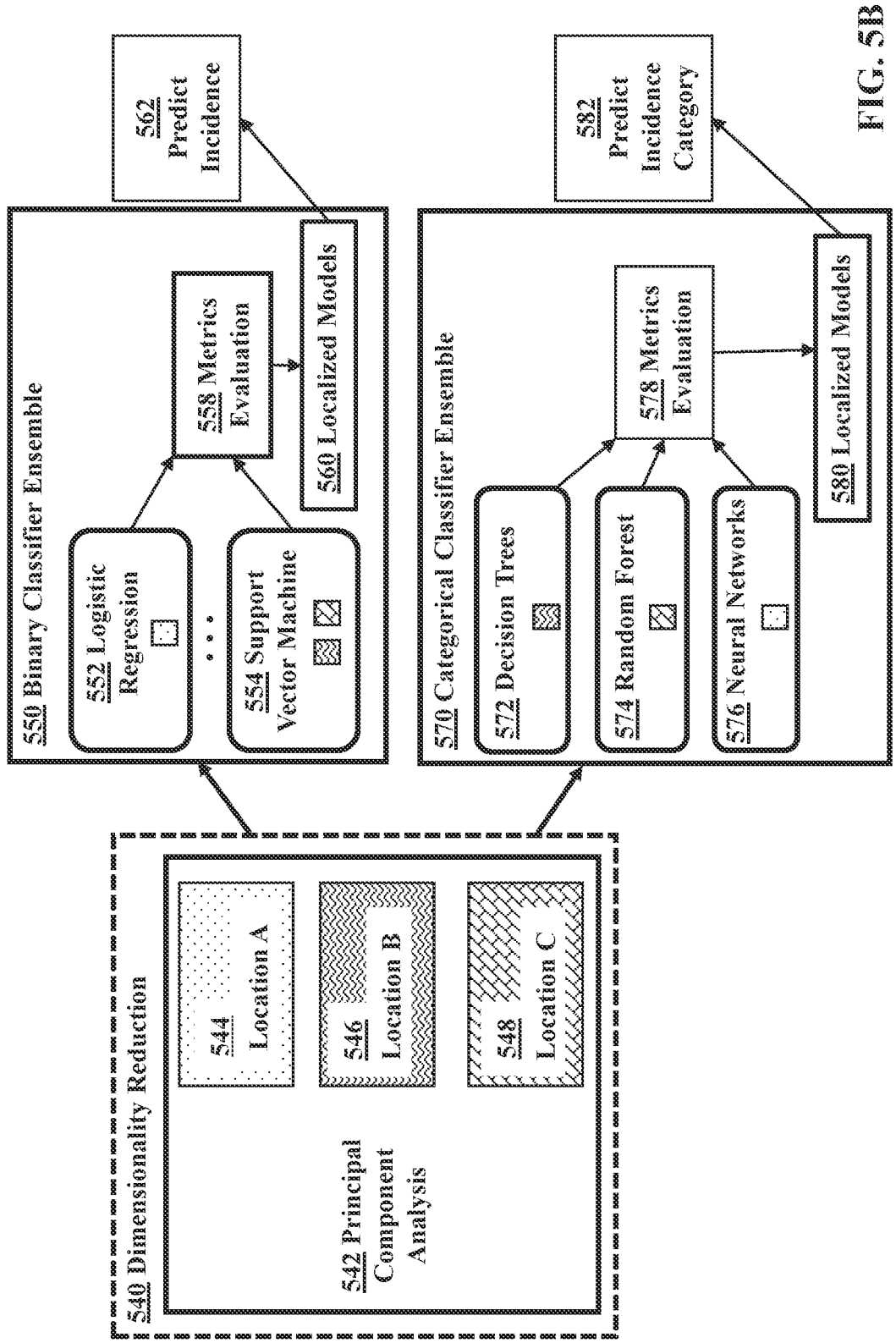
FIG. 5B illustrates a workflow for incident prediction in accordance with some embodiments of the present disclosure.

FIG. 5A and FIG. 5B depicts a workflow for incident prediction in accordance with some embodiments of the present disclosure. A fluid composition is obtained 506. A new component check 508 is performed. If no new constituent is identified, any known contaminants may be included in the identified contaminants 510. If a new constituent is identified, the properties may be extracted 532 (e.g., the chemical and microbial properties) and mapped to names 534. The mapping may use, for example, a Word2Vec algorithm to map new constituents to names based on the repository during natural language processing (NLP). Information for the mapping may be accessible via a repository of constituents and properties 536 which may communicate, directly or indirectly, with the name mapping mechanism. The mapping may then result in the identification of a new feature 538 which may then be included in identified contaminants 510.

Various data sources may be used to collect information about fluid quality. Information may be identified such as contaminants 510, weather conditions 512, medical statistics 514, user-related data 516 (e.g., regarding the consumers of a particular source), supply network 518, and/or one or more targets 520 (e.g., contaminant limits). Data may be collected regionally or globally; regional data may be submitted to a global database, and global data may be siphoned into a regional database, as desired.

Data from these sources may be submitted for dimensionality reduction 540. A principle component analysis 542 may be performed for each region. The principle component analysis 542 may analyze the data for location A 544, location B 546, and/or location C 548.

Analyzed data may be submitted to a classifier such as a binary classifier ensemble 550 and/or a categorical classifier ensemble 570. The binary classifier ensemble 550 may perform logistic regression 552 and/or support vector machine analysis 554, the metrics thereof may be evaluated 558 and compared to localized models 560 to predict incidence 562 (e.g., whether the water supply will have a harmful effect on a person consuming it).

The categorical classifier ensemble 570 may use decision trees 572, random forest 574, and/or neural networks 576, the metrics thereof may be evaluated 578 and compared to localized models 580 to predict incidence category 582 (e.g., what kind of incidence will occur if water is consumed from the water supply). The category of incidence may include, for example, whether the incidence is a viral or bacterial infection, or whether consumption may result in a person having high levels of indigestible inorganic compounds.

Figure 6:
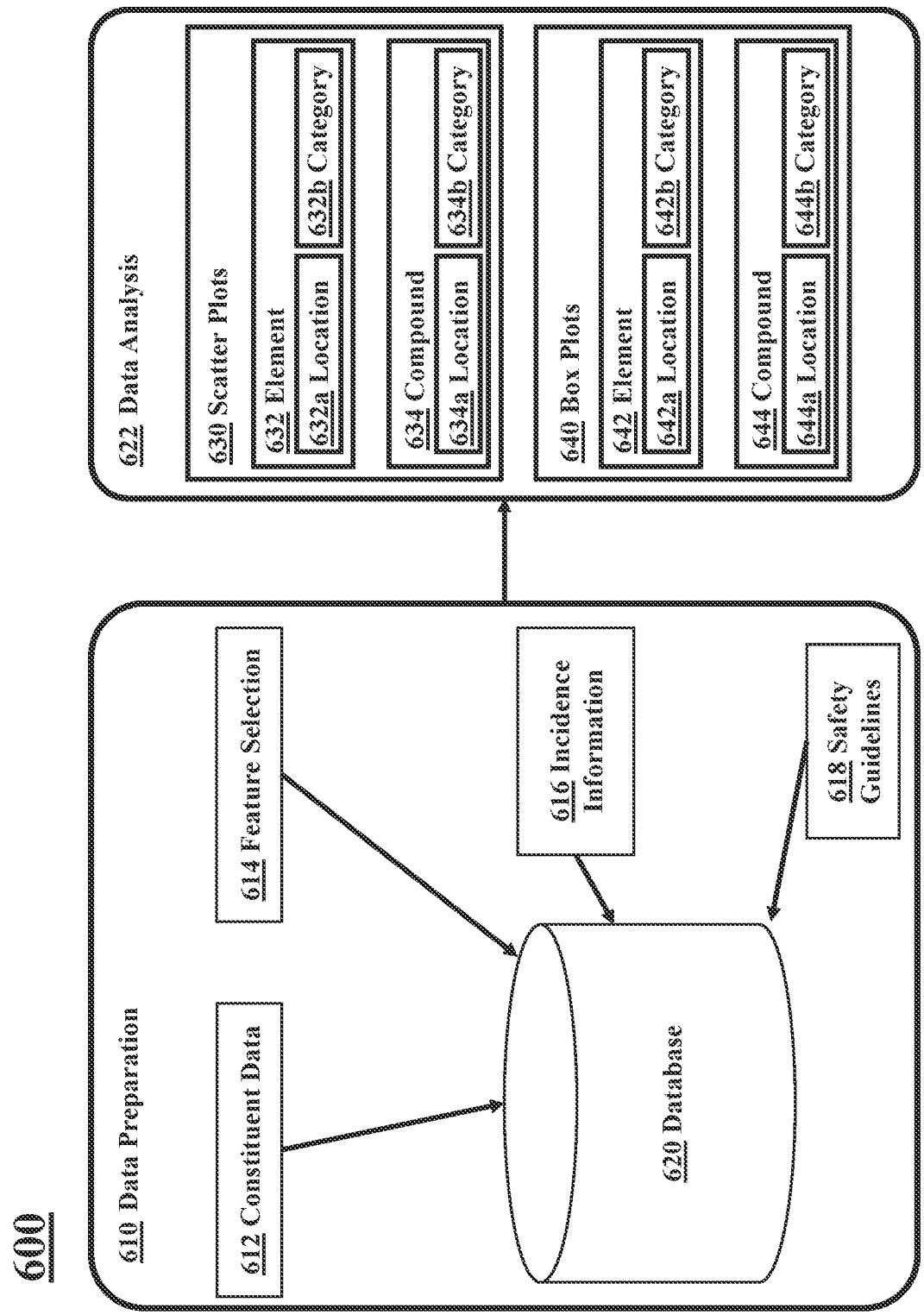
FIG. 6 depicts a workflow for incident prediction in accordance with some embodiments of the present disclosure.

FIG. 6 depicts a workflow for incident prediction 600 in accordance with some embodiments of the present disclosure. Data may be prepared and analyzed prior to submission to a classifier for classification. Data preparation 610 may include collecting data into a database 620. Data may include constituent data 612, feature selection 614, incidence information 616, safety guidelines 618, and other relevant data.

Prepared data may be submitted for data analysis 622. Data analysis 622 may include, for example, scatter plots 630 and box plots 640 for various elements 632 and 642 and various compounds 634 and 644. Elements 632 and 642 and compounds 634 and 644 may be analyzed based on location 632a, 634a, 642a, and 644a and category 632b, 634b, 642b, and 644b.

Figure 7:
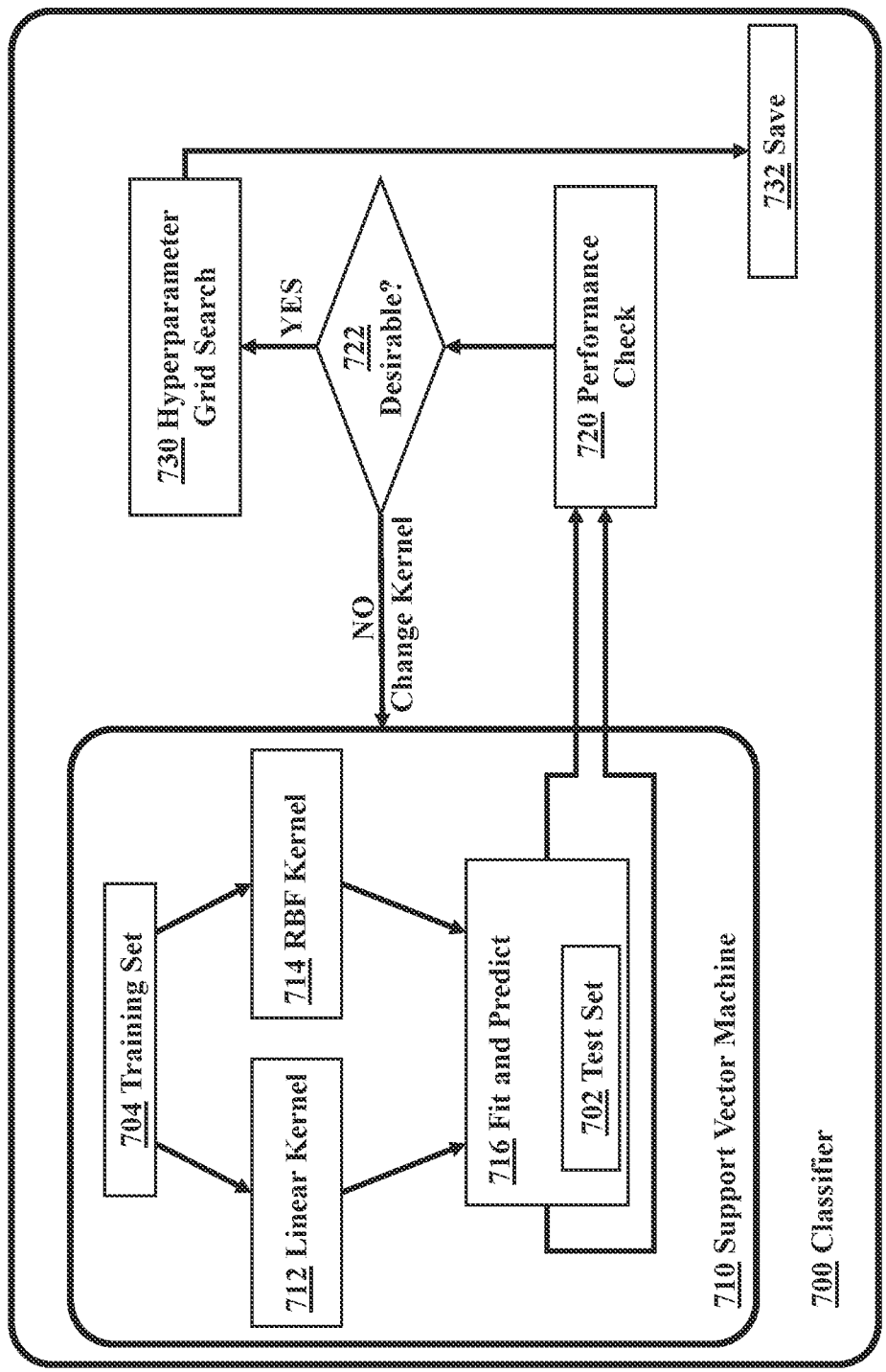
FIG. 7 illustrates a diagram of a classifier for a workflow for incident prediction in accordance with some embodiments of the present disclosure.

FIG. 7 illustrates a diagram of a classifier 700 for a workflow for incident prediction in accordance with some embodiments of the present disclosure. The classifier 700 uses a SVM 710; one skilled in the art will recognize that other classifiers (such as those discussed in FIG. 5B) may be used in accordance with the present disclosure. The SVM 710 uses a training set of data 704 to train a linear kernel 712 and a rational basis function kernel 714. The model is tested using a test set of data 702 for fit and prediction capability 716. A performance check 720 is conducted to identify whether the performance results are desirable 722. If the result is undesirable, the model may be rejected such that an alternative kernel is used. The result may be rejected as undesirable for any number of reasons as known in the art such as, for example, overfitting.

If the result of the performance check 720 and the results are desirable 722, a hyperparameter grid search may be performed 730. Specifically, a grid search of parameters C and gamma may be preferred; a preferred C may be approximately 10.0 and a preferred gamma may be approximately 1.0. The model may then be saved 732 for implementation.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment currently known or that which may be later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model with different physical and virtual resources dynamically assigned and reassigned according to demand. There is a sense of portion independence in that the consumer generally has no control or knowledge over the exact portion of the provided resources but may be able to specify portion at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but the consumer has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software which may include operating systems and applications. The consumer does not manage or control the underlying cloud infrastructure but has control over operating systems, storage, and deployed applications, and the consumer possibly has limited control of select networking components (e.g., host firewalls).

Deployment models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and/or compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
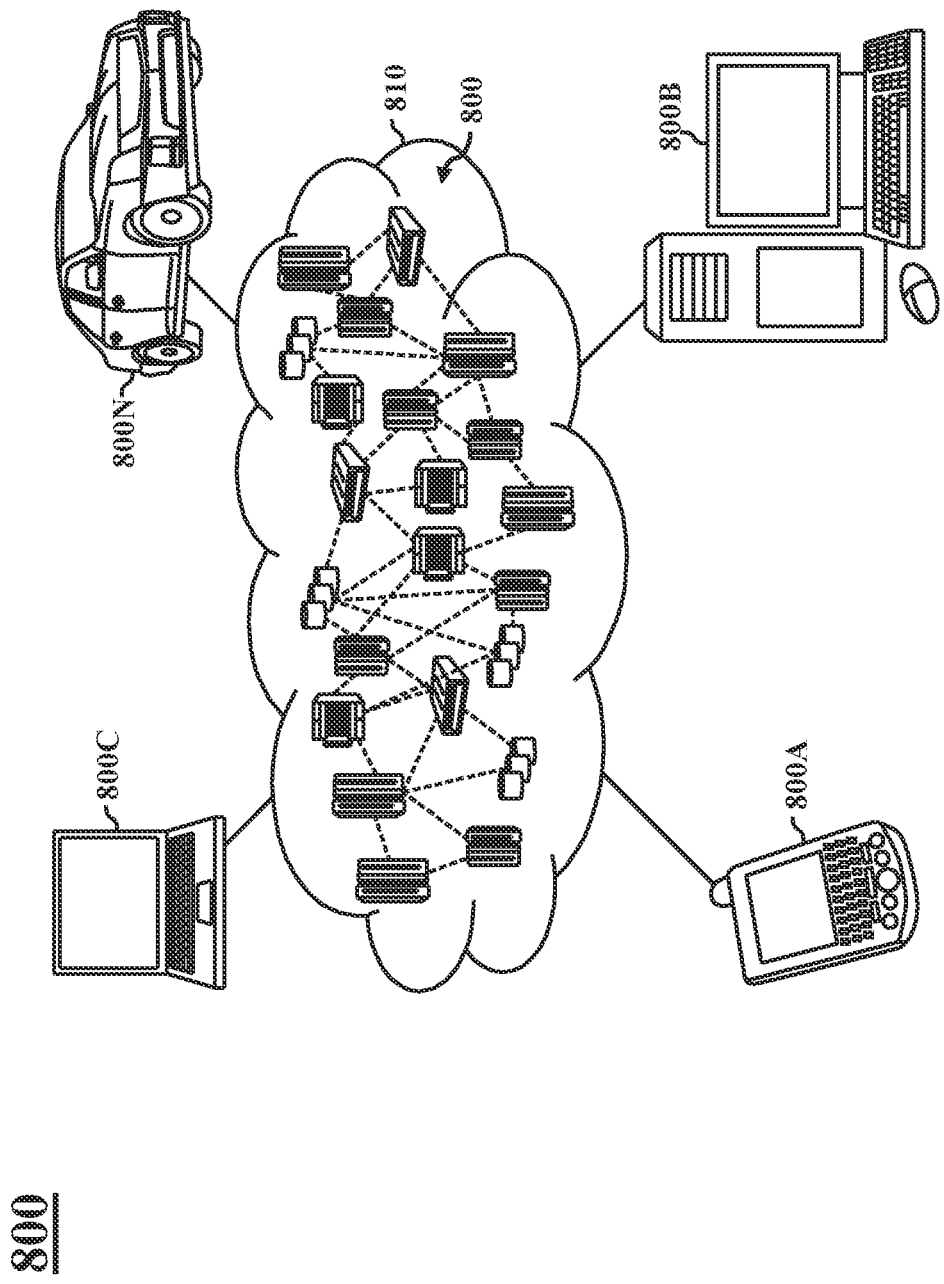
FIG. 8 depicts a cloud computing environment according to embodiments of the present disclosure.

FIG. 8 illustrates a cloud computing environment 810 in accordance with embodiments of the present disclosure. As shown, cloud computing environment 810 includes one or more cloud computing nodes 800 with which local computing devices used by cloud consumers such as, for example, personal digital assistant (PDA) or cellular telephone 800A, desktop computer 800B, laptop computer 800C, and/or automobile computer system 800N may communicate. Nodes 800 may communicate with one another. They may be grouped (not shown) physically or virtually, in one or more networks, such as private, community, public, or hybrid clouds as described hereinabove, or a combination thereof.

This allows cloud computing environment 810 to offer infrastructure, platforms, and/or software as services for which a cloud consumer does not need to maintain resources on a local computing device. It is understood that the types of computing devices 800A-N shown in FIG. 8 are intended to be illustrative only and that computing nodes 800 and cloud computing environment 810 can communicate with any type of computerized device over any type of network and/or network addressable connection (e.g., using a web browser).

Figure 9:
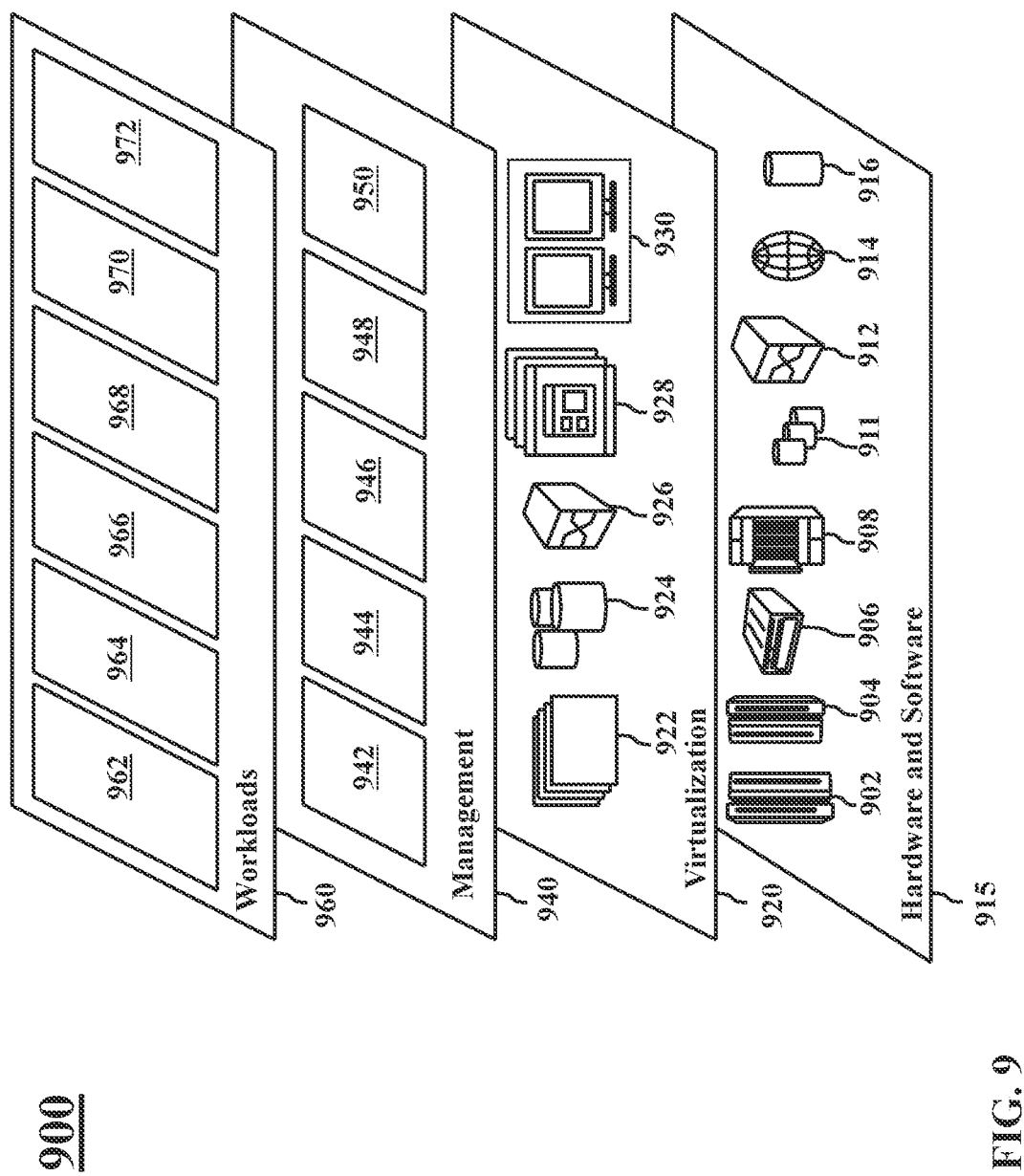
FIG. 9 illustrates abstraction model layers in accordance with embodiments of the present disclosure.

FIG. 9 illustrates abstraction model layers 900 provided by cloud computing environment 810 (FIG. 8) in accordance with embodiments of the present disclosure. It should be understood in advance that the components, layers, and functions shown in FIG. 9 are intended to be illustrative only and embodiments of the disclosure are not limited thereto. As depicted below, the following layers and corresponding functions are provided.

Hardware and software layer 915 includes hardware and software components. Examples of hardware components include: mainframes 902; RISC (Reduced Instruction Set Computer) architecture-based servers 904; servers 906; blade servers 908; storage devices 911; and networks and networking components 912. In some embodiments, software components include network application server software 914 and database software 916.

Virtualization layer 920 provides an abstraction layer from which the following examples of virtual entities may be provided: virtual servers 922; virtual storage 924; virtual networks 926, including virtual private networks; virtual applications and operating systems 928; and virtual clients 930.

In one example, management layer 940 may provide the functions described below. Resource provisioning 942 provides dynamic procurement of computing resources and other resources that are utilized to perform tasks within the cloud computing environment. Metering and pricing 944 provide cost tracking as resources and are utilized within the cloud computing environment as well as billing or invoicing for consumption of these resources. In one example, these resources may include application software licenses. Security provides identity verification for cloud consumers and tasks as well as protection for data and other resources. User portal 946 provides access to the cloud computing environment for consumers and system administrators. Service level management 948 provides cloud computing resource allocation and management such that required service levels are met. Service level agreement (SLA) planning and fulfillment 950 provide pre-arrangement for, and procurement of, cloud computing resources for which a future requirement is anticipated in accordance with an SLA.

Workloads layer 960 provides examples of functionality for which the cloud computing environment may be utilized. Examples of workloads and functions which may be provided from this layer include: mapping and navigation 962; software development and lifecycle management 964; virtual classroom education delivery 966; data analytics processing 968; transaction processing 970; and a predictive alerting system 972.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide, or other transmission media (e.g., light pulses passing through a fiber-optic cable) or electrical signals transmitted through a wire.

Computer readable program instructions described herein can be downloaded to respective computing/processing devices from a computer readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer, or entirely on a remote computer or server. In the latter scenario, the remote computer may be connected to the user's computer through any type of network, including a local area network (LAN) or a wide area network (WAN) or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus, or other device to produce a computer implemented process such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions which comprises one or more executable instructions for implementing the specified logical function(s). In some alternative implementations, the functions noted in the blocks may occur out of the order noted in the figures. For example, two blocks shown in succession may, in fact, be accomplished as one step, executed concurrently, substantially concurrently, in a partially or wholly temporally overlapping manner, or the blocks may sometimes be executed in the reverse order depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although the present disclosure has been described in terms of specific embodiments, it is anticipated that alterations and modification thereof will become apparent to the skilled in the art. The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application, or the technical improvement over technologies found in the marketplace or to enable others of ordinary skill in the art to understand the embodiments disclosed herein. Therefore, it is intended that the following claims be interpreted as covering all such alterations and modifications as fall within the true spirit and scope of the disclosure.

What is claimed is:

1. A system, said system comprising:
a memory; and
a processor in communication with said memory, said processor being configured to perform operations, said operations comprising:
  accepting fluid parameter data about a fluid, wherein said fluid is water;
  identifying a safety threshold for said fluid based on a fluid quality database, wherein said safety threshold includes a contaminant limit for a substance in said fluid;
  determining a fluid quality index for said fluid based on said fluid parameter data and said safety threshold;
  receiving fluid quality testing data for said fluid;
  comparing said fluid quality testing data to said fluid quality index to achieve a performance statistic; and
  leveraging said performance statistic to control a fluid flow; and
  triggering an action based on said performance statistic, wherein said action includes submitting a work order.

2. The system product of claim 1 further comprising:
identifying that said fluid quality testing data is not within said at least one safety threshold; and
stopping said fluid flow.

3. The system of claim 1 further comprising:
generating an alert based on said fluid quality testing data; and
publishing said alert.

4. The system of claim 1 further comprising:
calculating, using a machine learning model, said fluid quality testing data, wherein said machine learning model is trained using historical fluid quality testing data.

5. The system of claim 1 further comprising:
capturing current fluid parameter data with at least one fluid monitoring device.

6. A method, said method comprising:
accepting fluid parameter data about a fluid, wherein said fluid is water;
identifying a safety threshold for said fluid based on a fluid quality database, wherein said safety threshold includes a contaminant limit for a substance in said fluid;
determining a fluid quality index for said fluid based on said fluid parameter data and said safety threshold;
receiving fluid quality testing data for said fluid;
comparing said fluid quality testing data to said fluid quality index to achieve a performance statistic; and
leveraging said performance statistic to control a fluid flow; and
triggering an action based on said performance statistic, wherein said action is includes submitting a work order.

7. The method of claim 6 further comprising:
identifying that said fluid quality testing data is not within said safety threshold; and
stopping said fluid flow.

8. The method of claim 6 further comprising:
generating an alert based on said fluid quality testing data; and
publishing said alert.

9. The method of claim 8 wherein:
said alert identifies said performance statistic exceeds said safety threshold; and
said alert triggers a stoppage of said fluid flow.

10. The method of claim 6 further comprising:
calculating, using a machine learning model, said fluid quality testing data, wherein said machine learning model is trained using historical fluid quality testing data.

11. The method of claim 10 wherein:
said machine learning model calculates said fluid quality testing data in real time.

12. The method of claim 6 further comprising:
capturing current fluid parameter data with at least one fluid monitoring device.

13. The method of claim 12 wherein:
said at least one fluid monitoring device is a smart water meter.

14. A computer program product, said computer program product comprising a computer readable storage medium having program instructions embodied therewith, said program instructions executable by a processor to cause said processor to perform a function, said function comprising:
accepting fluid parameter data about a fluid, wherein said fluid is water;
identifying a safety threshold for said fluid based on a fluid quality database, wherein said safety threshold is a maximum acceptable risk of fluid contamination;
determining a fluid quality index for said fluid based on said fluid parameter data and said safety threshold;
receiving fluid quality testing data for said fluid;
comparing said fluid quality testing data to said fluid quality index to achieve a performance statistic; and
leveraging said fluid quality testing data to control a fluid flow; and
triggering an action based on said performance statistic, wherein said action includes submitting a work order.

15. The computer program product of claim 14 further comprising:
identifying that said fluid quality testing data is not within said safety threshold; and
stopping said fluid flow.

16. The computer program product of claim 14 further comprising:
generating an alert based on said fluid quality testing data; and publishing said alert.

17. The computer program product of claim 16 wherein:
said alert identifies said performance statistic exceeds said safety threshold; and
said alert triggers a stoppage of said fluid flow.

18. The computer program product of claim 14 wherein:
calculating, using a machine learning model, said fluid quality testing data, wherein said machine learning model is trained using historical fluid quality testing data.

19. The computer program product of claim 18 wherein:
said machine learning model calculates said fluid quality testing data in real time.

20. The computer program product of claim 14 further comprising:
capturing current fluid parameter data with at least one fluid monitoring device.

* * * * *